United States Patent [19]
Detty et al.

[11] Patent Number: 5,652,346
[45] Date of Patent: Jul. 29, 1997

[54] DICARBOXYLIC ACID OXIDATION PRODUCTS

[75] Inventors: Michael Ray Detty; Susan Jean Danielson, both of Rochester, N.Y.

[73] Assignee: Johnson & Johnson Clinical Diagnostics, Inc., Rochester, N.Y.

[21] Appl. No.: 613,812

[22] Filed: Mar. 6, 1996

Related U.S. Application Data

[63] Continuation of Ser. No. 558,919, Jul. 27, 1990, abandoned.

[51] Int. Cl.$^6$ .............................. C07G 3/00; C07G 17/00; C07H 1/00; C07H 15/00
[52] U.S. Cl. .................. 536/18.6; 536/1.11; 536/5; 536/4.1; 536/18.2; 536/18.5; 536/124
[58] Field of Search .................................. 536/18.6, 1.11, 536/5, 4.1, 18.2, 18.5, 124

[56] References Cited

U.S. PATENT DOCUMENTS

| | | | |
|---|---|---|---|
| 3,850,752 | 11/1974 | Schuurs et al. | 435/7.93 |
| 3,875,011 | 4/1975 | Rubenstein et al. | 435/188 |
| 3,997,525 | 12/1976 | Guy | 536/7 |
| 4,184,037 | 1/1980 | Wilkinson | 536/5 |

OTHER PUBLICATIONS

Rinehart, K.L., *Oxidation and Reduction of Organic Compounds*, 1973, pp. 68–72 and 80–82.

*Primary Examiner*—John Kight
*Assistant Examiner*—Louise Leary

[57] ABSTRACT

What is disclosed is a dicarboxylic acid oxidation product of a immunologically reactive mono- or a polysaccharide having vicinal diols.

8 Claims, No Drawings

DICARBOXYLIC ACID OXIDATION PRODUCTS

This is a continuation of application Ser. No. 07/558,919, filed Jul. 27, 1990 now abandoned.

FIELD OF THE INVENTION

This invention relates to a dicarboxylic acid oxidation product of a immunologically reactive mono- or a polysaccharide having vicinal diols and to a process for their preparation.

BACKGROUND OF THE INVENTION

Immunoassays, which take advantage of natural immunological reactions, have found widespread use as analytical techniques in clinical chemistry. Because of the specificity of the reactions, they are particularly advantageous in quantifying biological analytes (called ligands herein) which include, for example, antibodies therapeutic drugs, narcotics, enzymes, hormones, proteins, etc.

In competitive binding assays, a labeled ligand analog (sometimes referred to as ligand analog herein) is placed in competition with the unlabeled ligand for reaction with a fixed amount of the appropriate binding material (called a receptor herein). Unknown concentrations of the ligand can be determined from the measured signal of either the bound or unbound (i.e. free) ligand analog. The reaction proceeds as follows:

ligand+ligand analog+receptor ⇌ ligand-receptor+ligand-analog receptor.

The traditional approach to the preparation of labeled ligand analogs for haptens such as steroids which contain carbohydrate residues with vicinal diols on the terminal monosaccharide residues, involves the oxidation of the terminal monosaccharide residues of steroids to dialdehydes followed by attachment to amine residues of an enzyme label. The problem is that this approach has not generated satisfactory enzyme labeled ligand analogs for immunoassays. In such assays a substantial amount of the analog is not bound by antibody. Attempts to functionalize digoxigenin, the steroid component of digoxin, have met with limited success due to limited recognition of such functionalized material by the antibody. It would be desirable to have functionalized steroid derivatives such as digoxin that are easily bound to labels such as enzymes and that are recognized by antibodies for the steroid.

SUMMARY OF THE INVENTION

The present invention provides chemical compounds that are dicarboxylic acid oxidation products of immunologically reactive mono- or polysaccharides having vicinal diols. The following structure is representative of the oxidation product of this invention:

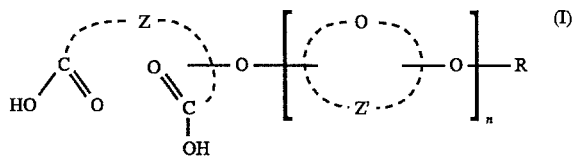

wherein;

R is an immunologically reactive group devoid of vicinal diol, carboxylic acid, primary amine and sulfhydryl groups;

Z represents the residual atoms of a saccharide group having dicarboxylic acid groups formed from the oxidation of the carbon atoms containing vicinal diol groups;

Z' represents the atoms necessary to complete a saccharide group; and n is an integer from 0 to about 2,500. Immunologically reactive group refers to residues of immunologically reactive species that exhibit specific binding with a receptor such as an antibody. Immunologically reactive analytes, also referred to as ligands, are included within this term. R includes the residue of a steroid group such as digoxin, digitoxin or ouabain. When n is greater than 1, the bracketed group represents a known polysaccharide nucleus (polysaccharides of up to 2,500 saccharide units are known; however this number may be higher since degradation during sample preparation occurs).

Although the R groups are "immunologically reactive" groups, saccharide groups can also function as immunologically reactive species. Therefore, for some uses the immunological activity of the R groups is predominant, for other uses the immunological activity of the saccharide groups is predominant, and in yet other uses, the immunological activity of both groups is desired. In the cases of digoxin and digitoxin assays, the latter situation wherein the immunological reactivity is derived from the combination of the steroid and saccharide groups, is preferred.

The compounds of this invention are useful as intermediates in the preparation of novel ligand analogs for immunoassays.

The present invention also provides a method of making the dicarboxylic acid oxidation product of this invention, comprising the steps of:

(a) providing a mono- or a polysaccharide having a group capable of specific binding with an immunologically reactive analyte (ligand) and two vicinal diols located on a terminal saccharide group; and (b) oxidizing said terminal saccharide at the vicinal diol portion with a mixture of periodic acid and chromium trioxide in aqueous mixtures of miscible organic solvents to produce the oxidation product.

DETAILS OF THE INVENTION

The combination of periodic acid and chromium trioxide have been utilized for the selective oxidation of compounds having vicinal diols to carboxylic acids in the presence of other primary and secondary alcohols and ketones. Oxidation does not occur at any sites other than at the vicinal diol sites with this reagent system. Therapeutically useful steroids such as digoxin, digitoxin and ouabain have vicinal diols in their terminal saccharide rings.

Mono- and polysaccharides, including mono- and trisaccharides, atetold or other biologically useful group, e.g., immunologically reactive group, are oxidized at the vicinal diol sites in the terminal saccharide by a mixture of periodic acid and chromium trioxide in aqueous dioxane to give carboxylic acid derivatives. The mixture of periodic acid and chromium dioxide has a molar concentration ratio in the range 4/1 to 1/1, preferably 2/1.

The oxidation can be carried out in aqueous mixtures of water-miscible organic solvents. Examples of water-miscible organic solvents include dioxane, methanol, ethanol, propanol, isopropanol, DMF, acetone, etc. Dioxane, acetone and DMF are preferred.

The polysaccharide chain can be linear or branched as is known in the art as long as the linkage that unites the monosaccharide units is a glycosidic bond. This bond can be α or β, and can join the reactive units through linkages that are 1,2, 1,3, 1,4 or 1,6 in the linear sequence, or between those units that are at branch points in the polymer (*Principles of Biochemistry*, A. White et al, 6th Ed., McGraw-Hill, Inc. New York, N.Y., page 33). Although the saccharide units which make up the polymer are generally derived from D-glucose, they can be derived from other monosaccharides which are known to have substituents including lower alkyl, hydroxy, hydroxymethyl, lower alkoxy, lower acyloxy, and lower alkanamido, exemplary units being those derived from D-mannose, D- and L-galactose, D-xylose and L-arabinose. Other units also occur as constituents of polysaccharides such as D-glucuronic, D-galacturonic and D-mannuronic acids. A great many polysaccharides have been described, thus many variants are possible.

Useful dicarboxylic acid oxidation products within structure I which can be made according to the described method include those having the structure:

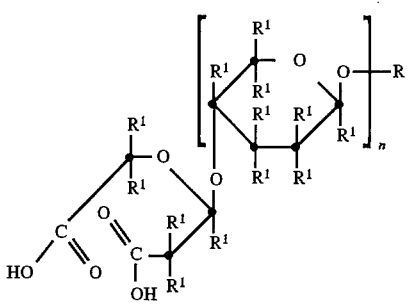
(Ia)

wherein

R and n are as previously defined;

$R^1$ each independently, represents hydrogen, lower alkyl, lower alkoxy, lower acyloxy, lower alkanamido, hydroxy or hydroxymethyl, in which "lower" refers to carbon chains of about 1 to 4 carbon atoms; and the linkages between monosaccharide units is an α or β glycosidic bond.

Other useful dicarboxylic acid oxidation products have the structure:

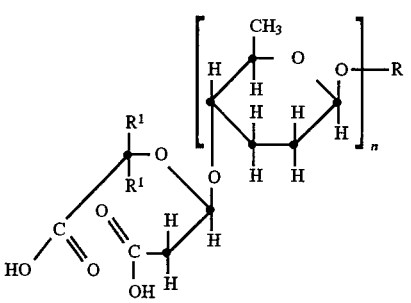
(Ib)

wherein;

R and $R^1$ are as previously defined and n is 0 to 3

Exemplary saccharides such as the steroids digoxin, digitoxin and ouabain were oxidized by the above method to give mixtures containing mono- and dicarboxylic acids:

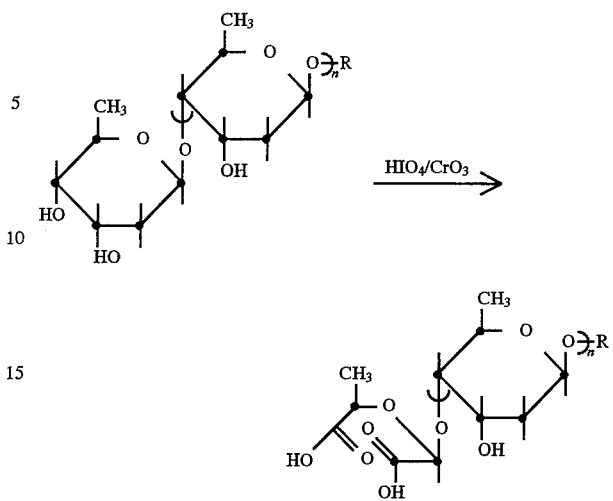

The immunologically reactive group R cannot contain vicinal diol groups, carboxylic acid groups (or equivalents thereof), primary amine, or sulfhydryl groups, as many immunologically reactive agents do, because vicinal diol groups would participate undesirably in the oxidation of step 2. The other named groups would participate in other unwanted condensation reactions, including self-crosslinking, in subsequent derivatizing (condensation) reactions used to append useful groups, such as labels, via the carboxy groups.

Examples of useful R groups include haptens such as hormones, vitamins, alkaloids, lipids mono- and/or polysaccharides and steroids (including steroid residues of digoxin, digitoxin and ouabain). R can be a component of physiological fluids, cell and tissue extracts, or a chemical compound that is capable of participating in an immunological reaction with a corresponding receptor compound (natural or synthetic). The receptor is a chemical or biological compound that has a reactive site for immunological reaction with R, the immunologically reactive group. By immunologically reactive group is meant substance which participates in an antigen-antibody reaction.

In addition, Structure I product can be attached to a polymer such as a protein which is then appended to polymer particles (beads) whereby the protein serves as a large linking group between the structure I product and the bead. The protein can serve other purposes such as improving aqueous and/or biological compatibility, as well as extending Structure I compounds away from the polymer particle to reduce stezic hindrance during use.

The following examples illustrate the method of making the compounds of Structure I.

EXAMPLE 1

Preparation of the Dicarboxylic Acid Oxidation Product of Digoxin

Periodic acid (6.84 g, 30.0 mmol) and chromium trioxide (1.50 g, 15.0 mmol) were added simultaneously to a slurry of digoxin (2.00 g, 2.56 mmol) in 150 mL of 50% aqueous dioxane cooled to 0° C. The resulting solution was stirred 1 hour at 0° C. The reaction mixture was poured into 500 mL of water. The products were extracted with ethyl acetate (3×75 mL). The combined organic extracts were washed with brine (3×100 mL), dried over sodium sulfate and concentrated. The residue was dissolved in 20 mL of hot ethyl acetate and then diluted with ether at ambient temperature until the solution became cloudy. Chilling precipitated a white powder which was collected by filtration, washed with ether, and dried to give the dicarboxylic acid oxidation product of digoxin. Yield 1.68 g (81%), mp 152°–155° C.: $^1$H NMR (D$_2$O, CDCl$_3$) δ 5.95 (s, 1H), 5.2–4.6 (m, 7H), 4.3–3.7 (m, 5H), 3.55 (m, 2H), 3.30 (m, 1H), 2.9–2.6 (m, 4H), 2.5–2.1 (m, 2H), 2.1–1.5 (m, 11H), 1.5–1.1 (m, 16H), 1.03 (s, 3H), 1.00 (s, 3H); $^{13}$C NMR (CDCl$_3$) δ 212.2, 205.4, 203.8, 202.3, 201.8, 175.3, 175.1, 174.4, 118.2, 100.3, 99.6, 99.5, 98.3, 86.5, 86.44, 84.3, 84.1, 78.1, 77.7, 74.0, 73.7, 73.6, 73.0, 71.2, 71.1, 64.1, 48.9, 46.2, 41.1, 39.8, 37.3, 36.4, 35.4, 33.4, 32.7, 29.9, 29.85, 29.8, 26.9, 26.3, 26.2, 26.15, 26.1, 23.2, 21.8, 18.9, 18.6, 18.6, 18.55, 18.53, 18.45, 16.5, 15.1.

EXAMPLE 2

Preparation of the Dicarboxylic Acid Oxidation Product of Digitoxin

Periodic acid (6.84 g, 30.0 mmol) and chromium trioxide (1.50 g, 15.0 mmol) were added simultaneously to a slurry of digitoxin (2.00 g, 2.61 mmol) in 150 mL of 50% aqueous dioxane cooled to 0° C. The resulting solution was stirred 1 hour at 0° C. and then allowed to warm to ambient temperature. The solution was poured into 500 mL of water. The product was extracted with ethyl acetate (3×75 mL). The combined organic extracts were washed with brine (3×100 mL), dried over sodium sulfate, and concentrated. The residue was dissolved in 20 mL of hot ethyl acetate and then diluted with pentane at ambient temperature until the solution became cloudy. Chilling precipitating a white powder which was collected by filtration, washed with pentane and dried. Yield 1.55 g (75%), mp 135°–145° C.: $^1$H NMR (CDCl$_3$) δ 5.90 (s, 1H), 5.18 (m, 1H), 5.01 (d, 1H), 4.98 (br s, 1H), 4.83 (br s, 1H), 4.81 (d, 1H), 4.79 (m, 1H), 4.50 (br, 5H), 4.23 (d, 1H), 4.10 (br s, 1H), 3.96 (d, 1H), 3.64 (m, 1H), 3.58 (m, 1H), 2.78 (m, 6H), 2.15 (m, 2H), 1.87 (m, 2H), 1.8–1.3 (m, 19H), 1.25 (m, 9H), 0.95 (s, 3H), 0.90 (s, 3H).

EXAMPLE 3

Preparation of the Dicarboxylic Acid Oxidation Product of Ouabain

Periodic acid (4.56 g, 20.0 mmol) and chromium trioxide (1.00 g, 10.0 mmol) were added simultaneously to a stirred slurry of ouabain (1.00 g, 1.37 mmol) in 50 mL of 50% aqueous dioxane cooled to 0° C. The resulting solution was stirred 1 hour at 0° C. and then allowed to warm to ambient temperature. The reaction mixture was poured into 200 mL of water. The products were extracted with ethyl acetate (3×50 mL). The combined organic extracts were washed with brine (5×50 ml) until colorless, dried over sodium sulfate, and concentrated. The residue was dissolved in 5 mL of hot ethyl acetate and diluted with ether at ambient temperature until the solution became cloudy. Chilling precipitated a white powder which was collected by filtration, washed with ether, and dried. Yield 0.13 g (13%), mp 135°–139° C.

The structure I products are useful as intermediates in the preparations of ligand analogs used in immunoassays. The ligands are prepared by condensing the Structure I product, or an equivalent thereof, i.e. the acid halide, ester, anhydride, etc. thereof, with a label or support containing a primary or secondary amino or sulfhydryl group to produce a ligand analog.

The following examples 5–7 use Structure I products of Examples 1–3, as intermediates in the preparation of the titled labeled ligand analogs.

EXAMPLE 4

Preparation of Horseradish Peroxidase (HRP) Labeled Digoxin Analog

The oxidized digoxin from Example 1 (102 mg, 1.25×10$^{-4}$ mol) was dissolved in 2.5 mL of dry N,N-dimethylformamide (DMF). Tributylamine (23 µL, 1.25×10$^{-4}$ mol) was added and the resulting solution was cooled in an ice bath. Isobutyl chloroformate (17.1 µL, 1.25×10$^{-4}$ mol) was added and the resulting solution was stirred for 20 minutes at 0° C.

Deionized distilled water was added to 50 mg (1.25×10$^{-6}$ mol) of HRP to a volume of 25 mL. The pH of this solution was adjusted to 9.0 with dilute sodium hydroxide solution. The solution containing the oxidized digoxin was added dropwise to the solution containing the HRP while the pH was maintained at 9.0. After addition was complete, stirring at pH 9 was continued for 1.5 hours, and then the pH was lowered to 7.0 with dilute hydrochloric acid. Hydroxylamine was added to a final concentration of 0.020M and the resulting solution was stirred for 2 hours. The reaction mixture was dialyzed against 3 L of 0.02M MOPS, pH 7.0, overnight with the dialysis buffer being changed once during this period. The label was purified by Eel filtration (Bio-Gel P-2, 200–400 mesh) eluting with 0.02M MOPS, pH 7.0. Merthiolate (0.01%) was added as a preservative.

EXAMPLE 5

Preparation of Amine-Enriched HRP Labeled Digitoxin Analog

The oxidized digitoxin from Example 2 (100 mg, 1.25×10$^{-4}$M) was dissolved in 2.5 mL of dry N,N-dimethylformamide (DMF). Tributylamine (23 µL, 1.25×10$^{-4}$ mol) was added and the resulting solution was cooled in an ice bath. Isobutyl chloroformate (17.1 µL, 1.25×10$^{-4}$ mol) was added and the resulting solution was stirred for 20 minutes at 0° C.

Amine enriched HRP was prepared as follows. HRP (200 mg) was dissolved in 40 mL of deionized distilled water. Ten mL of freshly made 0.1M sodium periodate in water was added and the resulting solution was stirred in the dark for 20 minutes. The reaction mixture was dialyzed overnight against 0.001M sodium acetate buffer (pH 4.0). Lysyl-lysine bishydrochloride salt (0.868 g, 12.5 mmol) was dissolved in 50 mL of 0.1M sodium carbonate (pH 9.5). The oxidized HRP solution was added and the resulting solution was stirred for 1 hour at ambient temperature. The pH was lowered to 8.0 and sodium cyanoborohydride (100 mg) was added. Stirring was continued for 3 hours. Glycine (1.5 g) and an additional 100 mg of sodium cyanoborohydride were added with stirring for an additional 3 to 4 hours. The reaction mixture was dialyzed against 0.02M 3-N-morpholinopropane sulfonic acid (MOPS, pH 7.0) changing the dialysis buffer twice over a 14 hour period. The amine-enriched HRP was purified by size exclusion chromatography when necessary to remove any HRP aggregates. Merthiolate (0.02%) was added as a preservative.

Deionized distilled water was added to 50 mg (1.25×10$^{-6}$ mol) of the amine-enriched HRP to a volume of 25 mL. The pH of this solution was adjusted to 9.0 with dilute sodium hydroxide solution. The solution containing the oxidized digitoxin was added dropwise to the solution containing the amine-enriched HRP while the pH was maintained at 9.0. After addition was complete, stirring was continued at pH 9, and then the pH was lowered to 7.0 with dilute hydrochloric acid. Hydroxylamine was added to a final concentration of 0.020M and the resulting solution was stirred for 2 hours. The reaction mixture was dialyzed against 3 L of 0.02M MOPS, pH 7.0, overnight with the dialysis buffer being changed once during this period. The label was purified by gel filtration (Bio-Gel P-2, 200–400 mesh) eluting with 0.02M MOPS, pH 7.0. merthiolate (0.01%) was added as a preservative.

EXAMPLE 6

Preparation of Alkaline Phosphatase (ALP) Labeled Digoxin Analog

The oxidized digoxin from Example 1 (20.3 mg, $2.5 \times 10^{-5}$ mol) was dissolved in 2.5 mL of dry N,N-dimethylformamide (DMF). Tributylamine (4.6 μL, $2.5 \times 10^{-5}$ mol) was added and the resulting solution was cooled in an ice bath. Isobutyl chloroformate (3.42 μL, $2.5 \times 10^{-5}$ mol) was added and the resulting solution was stirred for 20 minutes at 0° C.

Deionized distilled water was added to 25 mg ($2.5 \times 10^{-7}$ mol) of ALP to a volume of 25 mL. The pH of this solution was adjusted to 9.0 with dilute sodium hydroxide solution. The solution containing the oxidized digoxin was added dropwise to the solution containing the ALP while the pH was maintained at 9.0. After addition was complete, stirring at pH 9.0 was continued for 1.5 hours and then the pH was lowered to 7.0 with dilute hydrochloric acid. Hydroxylamine was added to a final concentration of 0.020M and the resulting solution was stirred for 2 hours. The reaction mixture was dialyzed against 3 L of phosphate buffered saline (PBS) overnight with the dialysis buffer being changed once during this period. The label was purified by gel filtration (Bio-Gel P-2, 200–400 mesh) eluting with PBS. The protein containing fractions were dialyzed against 0.05M tris(hydroxymethyl)aminomethane (TRIS), pH 8.0, containing 0.001M magnesium chloride and 0.0001M zinc chloride. The dialysis buffer was changed once. Sodium azide (0.02%) was added as a preservative and the label was stored in the dark at 4° C.

EXAMPLE 7

Preparation of ALP Labeled Digitoxin Analog

The oxidized digitoxin from Example 2 (19.9 mg, $2.5 \times 10^{-5}$ mol) was dissolved in 2.5 mL of dry N,N-dimethylformamide (DMF). Tributylamine (4.6 μL, $2.5 \times 10^{-5}$ mol) was added and the resulting solution was cooled in an ice bath. Isobutyl chloroformate (3.42 μL, $2.5 \times 10^{-5}$ mol) was added and the resulting solution was stirred for 20 minutes at 0° C.

Deionized distilled water was added to 25 mg ($2.5 \times 10^{-7}$ mol) of ALP to a volume of 25 mL. The pH of this solution was adjusted to 9.0 with dilute sodium hydroxide solution. The solution containing the oxidized digitoxin was added dropwise to the solution containing the ALP while the pH was maintained at 9.0. After addition was complete, stirring at pH 9.0 was continued for 1.5 hours and then the pH was lowered to 7.0 with dilute hydrochloric acid. Hydroxylamine was added to a final concentration of 0.020M and the resulting solution was stirred for 2 hours. The reaction mixture was dialyzed against 3 L of phosphate buffered saline (PBS) overnight with the dialysis buffer being changed once during this period. The label was purified by gel filtration (Bio-Gel P-2, 200–400 mesh) eluting with phosphate buffered saline. the protein containing fractions were dialyzed against 0.05M tris(hydrorymethyl) aminomethane (TRIS), pH 8.0, containing 0.001M magnesium chloride and 0.0001M zinc chloride. The dialysis buffer was changed once. Sodium azide (0.02%) was added as a preservative and the label was stored in the dark at 4° C.

The invention has been described in detail with particular reference to preferred embodiments thereof, but it will be understood that variations and modifications can be effected within the spirit and scope of the invention.

We claim:

1. A method of making a chemical compound that is a dicarboxylic acid oxidation product of an immunologically reactive mono- or a polysaccharide having vicinal diols, comprising the steps of:

(a) providing a mono- or a polysaccharide having a group capable of specific binding with an immunologically reactive analyte (ligand) and two vicinal diols located on a terminal saccharide group; and (b) oxidizing said terminal saccharide at the vicinal diol portion with a mixture of periodic acid and chromium trioxide in aqueous mixture containing a miscible organic solvent to produce the dicarboxylic acid oxidation product.

2. The method of claim 1 wherein the dicarboxylic acid oxidation product represented by the structure:

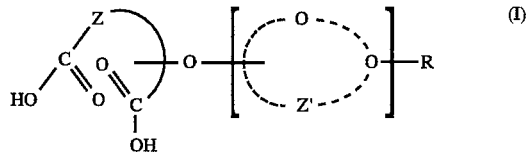

wherein;

R is an immunologically reactive group devoid of vicinal diol, carboxylic acid, primary amine and sulfhydryl groups;

Z represents the residual atoms of a saccharide group having dicarboxylic acid groups formed from the oxidation of the carbon atoms containing vicinal diol groups;

Z' represents the atoms necessary to complete a saccharide group; and n is an integer from 0 to about 2,500.

3. The method of claim 2 wherein the dicarboxylic acid oxidation product has the structure:

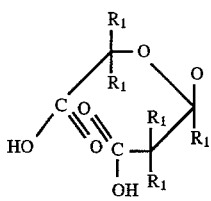

wherein;

R is an immunologically reactive group devoid of vicinal diol, carboxylic acid, primary amine and sulfhydryl groups;

$R^1$, each independently, represents hydrogen, lower alkyl, lower alkoxy, lower alkanamido, hydroxy or hydroxymethyl, in which "lower" refers to carbon chains of about 1 to 4 carbon atoms;

the linkages between monosaccharide units is an α or β glycosidic bond; and n is an integer from 0 to about 2,500.

4. The method of claim 3 wherein R is a steroid group.

5. The method of claim 4 wherein the steroid group is selected from the group consisting of digoxin, digitoxin or ouabain.

6. The method of claims 1, 2, 3, 4 or 5 wherein the mixture of periodic acid and chromium dioxide has a molar concentration ratio in the range of 4/1 to 1/1.

7. The method of claim 6 wherein the ratio is 2/1.

8. The method of claim 7 wherein the water miscible organic solvent is selected from the group consisting of dioxane, methanol, ethanol, propanol, isopropanol, DMF and acetone.

* * * * *